US009659358B2

(12) United States Patent
Sasamoto et al.

(10) Patent No.: US 9,659,358 B2
(45) Date of Patent: May 23, 2017

(54) APPARATUS FOR CHECKING ADHERENCE STATE OF FIBER REINFORCED PLASTIC TAPE

(71) Applicant: TORAY ENGINEERING CO., LTD., Chuo-ku, Tokyo (JP)

(72) Inventors: Hiromichi Sasamoto, Moriyama (JP); Hisashi Kobayashi, Otsu (JP); Yoshio Nogami, Kuwana (JP)

(73) Assignee: TORAY ENGINEERING CO., LTD., Tokyo (JP)

( * ) Notice: Subject to any disclaimer, the term of this patent is extended or adjusted under 35 U.S.C. 154(b) by 203 days.

(21) Appl. No.: 14/653,053

(22) PCT Filed: Dec. 3, 2013

(86) PCT No.: PCT/JP2013/082429
§ 371 (c)(1),
(2) Date: Jun. 17, 2015

(87) PCT Pub. No.: WO2014/103625
PCT Pub. Date: Jul. 3, 2014

(65) Prior Publication Data
US 2015/0348255 A1   Dec. 3, 2015

(30) Foreign Application Priority Data
Dec. 25, 2012   (JP) .................. 2012-281209

(51) Int. Cl.
*G01N 21/95* (2006.01)
*H04N 7/18* (2006.01)
(Continued)

(52) U.S. Cl.
CPC ....... *G06T 7/0004* (2013.01); *G01N 21/8806* (2013.01); *G01N 21/95* (2013.01);
(Continued)

(58) Field of Classification Search
None
See application file for complete search history.

(56) References Cited

U.S. PATENT DOCUMENTS 3,247,962 A * 4/1966 Obenshain ............. B65H 29/51
209/3.1
4,189,335 A * 2/1980 Evans ................ G01B 11/0616
156/64
(Continued)

FOREIGN PATENT DOCUMENTS

JP   S55-46188 A   3/1980
JP   08-261952 A   10/1996
(Continued)

OTHER PUBLICATIONS

International Search Report of the corresponding International Application No. PCT/JP2013/082429, dated Mar. 11, 2014.

*Primary Examiner* — Reza Aghevli
(74) *Attorney, Agent, or Firm* — Global IP Counselors, LLP

(57) ABSTRACT

An apparatus for checking an adherence state of fiber reinforced plastic tape includes an illuminating section having first and second illuminating groups. The main optical axes of illumination light beams of light emitting sections of the first illuminating group are set at a designated inclination angle with respect to a surface of an imaging region and distances on the main optical axes between a surface of a structural object and each of the light emitting sections are set to be the same. The main optical axes of illumination light beams of light emitting sections of the second illuminating group are set at an inclination angle different from the first illuminating group with respect to the surface of the imaging region and distances on the main optical axes
(Continued)

between the surface of the structural object and each of the light emitting sections are set to be the same.

9 Claims, 9 Drawing Sheets

(51) Int. Cl.
    *G01N 21/88*     (2006.01)
    *G06T 7/00*     (2017.01)
    *H04N 5/225*     (2006.01)
    *G01N 21/84*     (2006.01)

(52) U.S. Cl.
    CPC ....... *H04N 7/18* (2013.01); *G01N 2021/8472* (2013.01); *H04N 5/2256* (2013.01)

(56) References Cited

U.S. PATENT DOCUMENTS 5,694,979 A * 12/1997 Toda .................. D03J 1/00
                                                    139/1 B 2002/0106213 A1*   8/2002  Higeta ................. G03G 21/181
                                                399/104
2004/0130072 A1*   7/2004  Sekido ................. B29C 70/443
                                                264/408
2007/0097359 A1    5/2007  Engelbart et al.
2007/0223802 A1*   9/2007  Tateda .................... B29C 70/54
                                                382/141
2008/0204725 A1    8/2008  Fujii et al.

FOREIGN PATENT DOCUMENTS

| | | | | |
|---|---|---|---|---|
| JP | 2001-194314 | * | 1/2000 | ........... G01N 21/898 |
| JP | 2001-194314 A | | 7/2001 | |
| JP | 2007-256119 A | | 10/2007 | |
| JP | 2009-513984 A | | 4/2009 | |
| JP | 2011-085468 | * | 10/2009 | ........... G01N 21/892 |
| JP | 2011-085468 A | | 4/2011 | |
| JP | 4691562 B2 | | 6/2011 | |
| WO | 2012-039298 A1 | | 3/2012 | |

* cited by examiner

APPARATUS FOR CHECKING ADHERENCE STATE OF FIBER REINFORCED PLASTIC TAPE

CROSS-REFERENCE TO RELATED APPLICATIONS

This application is a U.S. National stage of International Application No. PCT/JP2013/082429 filed on Dec. 3, 2013. This application claims priority to Japanese Patent Application No. 2012-281209 filed with Japan Patent Office on Dec. 25, 2012. The entire disclosure of Japanese Patent Application No. 2012-281209 is hereby incorporated herein by reference.

BACKGROUND

Field of the Invention

The present invention relates to an apparatus for checking the adherence state of fiber reinforced plastic tape which is adhered by a plurality being lined up on the surface of a structural object.

Background Information

In recent years, fiber reinforced plastic materials are used for space flight applications and sports application where light weight and high performance of structural objects are in demand. In particular, a large number of sheet mold intermediate materials with a semi-hardened state, where carbon fibers are immersed in a thermosetting resin, which is referred to as prepreg, are adopted in space flight applications. Molding of the prepreg is performed by hardening using heat after multiple layers are laminated on the structural object.

Furthermore, it is easy for wrinkles to occur in the prepreg when attempting to adhere the prepreg with a wide sheet shape so as to follow along the surface shape of the structural object which is curved in a case of forming a surface which is curved such as a cylinder which is represented by the body of a plane. For this reason, in a case where prepreg is adhered and laminated on a surface which is curved, a technique is adopted where slits are appropriately cut into a sheet, and the sheet is adhered as a narrow tape shape and uniformly laminated.

In addition, strength in the prepreg differs between a direction in which the fibers extend and a direction which intersects with the fibers. For this reason, when adhering and laminating at a body section of a plane, laminating is carried out with the orientation necessarily being changed by 45 degrees or more compared to the lower layer so that the directions in which the fibers extend are vertical, diagonal, horizontal, and diagonal, and the laminating is performed over several tens of layers to around 100 layers. In addition, it is typical for the prepreg which is adhered in one layer to be adhered with several or around 50 strips being lined up at one time.

Then, checking of the adherence state is performed such as whether the prepreg which is adhered with a narrow tape shape as described above is lined up with a designated interval between each or does not overlapped with each other. The checking is performed using the human eye, but automatic checking is also proposed (for example, Japanese Patent No. 4691562 (Patent Literature 1) and Japanese Translation of PCT International Application Publication No. 2009-513984 (Patent Literature 2)) from the point of view of securing experts, faster checking times, reproducing checking quality, and the like.

SUMMARY

After the adhering of one layer of the prepreg tape is complete, checking is performed with regard to the adherence state of one layer of the prepreg tape which is adhered immediately beforehand before performing adhering of the next layer of the prepreg tape. For this reason, it is possible to shorten production lead time by shortening the time which is taken by the checking. For this reason, in attempting to achieve a shortening of the checking time using automatic checking, it is necessary for the field of view for simultaneous imaging to be widened and for the adherence state of a plurality of strips of the prepreg tape to be simultaneously checked.

However, when attempting to check the intervals between a plurality of strips of the prepreg tape using a line sensor, it is not possible to obtain desired checking results in a case of using bar illumination $30z$ which is arranged to be parallel to an imaging section $2z$ where a line sensor $20z$ is used as shown in FIG. 10. The reason is because, although the illumination light which is radiated from the bar illumination $30z$ radiates light which is parallel or which has an angle with a designated width from a direction where a main optical axis $32z$ is orthogonal with regard to the longitudinal direction (X direction) of the line sensor $20z$ (that is, the fiber direction in the prepreg tape is the Y direction), it is not possible to obtain sufficient contrast which is necessary in order to detect the edge position of the tape in the case of this aspect.

In addition, the checking results differ if the positions inside the field of view differ in a case where the light emission plane is arranged to be inclined with regard to the checking target object using surface illumination as shown in Patent Literature 1. The reason is because of non-uniformity of illumination within the field of view for imaging (for example, a peripheral section is darker with regard to a central section, the brightness differs on the left side and right side, and the like). This causes the intensity of light which is illuminated onto an imaging region to differ since the distances from the light emitting section to each point on the imaging region differ.

Therefore, the present invention is carried out by considering the problems described above and the object of the present invention is to propose an apparatus which is able to swiftly check due to it being possible to obtain the same checking results even when positions within the field of view differ for the adherence state of fiber reinforced plastic tape (that is, prepreg tape) which is adhered by a plurality being lined up on the surface of a structural object.

In order to solve the problems described above, the invention according a first aspect is an apparatus for checking the adherence state of fiber reinforced plastic tape, which is adhered by a plurality being lined up on the surface of a structural object, which is provided with an imaging section which images an imaging region with a line shape which is set on the fiber reinforced plastic tape, an illuminating section which radiates illumination light toward the imaging region, a checking section which checks the adherence state of the fiber reinforced plastic tape based on an image which is imaged using the imaging section, and a moving section which relatively moves the illuminating section and the imaging section with regard to the fiber reinforced plastic tape which is adhered, where the imaging section is provided with a line sensor where a plurality of light detection elements are aligned in a direction which intersects with the relative movement direction, the illuminating section is provided with a first illuminating group which is provided with a plurality of light emitting sections which are arranged to line up in a direction which intersects with the fiber direction of the fiber reinforced plastic tape, the first illuminating group is such that main optical axes of the illumination light beams which are radiated from each of the light emitting sections are set at a designated inclination angle with regard to the surface of the imaging region and the distances on the main optical axes between the surface of the structural object and each of the light emitting sections are set to be the same, the illuminating section is provided with a second illuminating group which is provided with a plurality of light emitting sections which are arranged to line up in a direction which intersects with the fiber direction of the fiber reinforced plastic tape, and the second illuminating group is such that the main optical axes of the illumination light beams which are radiated from each of the light emitting sections are set at an inclination angle, which is different to the first illuminating group, with regard to the surface of the imaging region and the distances on the main optical axes between the surface of the structural object and each of the light emitting sections are set to be the same.

The invention according to a second aspect is the apparatus for checking the adherence state of fiber reinforced plastic tape according to the first aspect, where each of the light emitting sections in the first illuminating group and each of the light emitting sections in the second illuminating group are set to be parallel to the surface of the imaging region, the main optical axes of each of the light emitting sections in the first illuminating group are set to be parallel to each other, and the main optical axes of each of the light emitting sections in the second illuminating group are set to be parallel to each other.

The invention according to a third aspect is the apparatus for checking the adherence state of fiber reinforced plastic tape according to the second aspect, where a focusing optical element is provided in the imaging section and at least the fiber reinforced plastic tape side of the focusing optical element is a telecentric focusing optical element.

The invention according to a fourth aspect is the apparatus for checking the adherence state of fiber reinforced plastic tape according to the first aspect, where a focusing optical element is provided in the imaging section, at least the fiber reinforced plastic tape side of the focusing optical element is a non-telecentric focusing optical element, and each of the light emitting sections in the first illuminating group and each of the light emitting sections in the second illuminating group are set at inclination angles so that the reflection peaks of the illumination light beams are the same for each of the fibers in the fiber reinforced plastic tape during imaging using the imaging section.

The invention according to a fifth aspect is the apparatus for checking the adherence state of fiber reinforced plastic tape according to any one of the first to fourth aspects, where the illuminating section is configured so that the illumination light beams radiate from an opening section which is provided in one section of a casing, each of the light emitting sections in the first illuminating group are each configured by a plurality of light emitting diodes which are arranged to line up in one row so that the distances to the checking region are equal in a state of being inclined with regard to the surface of the checking region from the opening section, and each of the light emitting sections in the second illuminating group are each configured by a plurality of light emitting diodes which are arranged to line up in one row so that the distances to the checking region are equal in a state of being inclined with regard to the surface of the checking region from the opening section.

The invention according to a sixth aspect is the apparatus for checking the adherence state of fiber reinforced plastic tape according to any one of the first to fourth aspects, where the illuminating section is provided with a plurality of opening sections which are provided in one section of a casing, each of the light emitting sections in the first illuminating group and each of the light emitting sections in the second illumination are configured so that one edge sides of branched optical fibers are connected with the plurality of opening sections, each of the light emitting sections in the first illuminating group are each configured to be arranged to line up in one row so that the distances to the checking region are equal in a state of being inclined with regard to the surface of the checking region from the opening sections, and each of the light emitting sections in the second illuminating group are each configured to be arranged to line up in one row so that the distances to the checking region are equal in a state of being inclined with regard to the surface of the checking region from the opening sections.

It is possible to swiftly check due to it being possible to obtain the same checking results even when positions within the field of view differ for the adherence state of fiber reinforced plastic tape which is adhered by a plurality being lined up on the surface of a structural object.

DETAILED DESCRIPTION OF EMBODIMENTS

An apparatus (referred to below as a checking apparatus) for checking the adherence state of fiber reinforced plastic tape (that is, prepreg tape with cases of being referred to below simply as tape) according to the present invention will be described below using FIG. 1. Here, in the description, the surface of an imaging region of a checking target object is expressed as the X and Y directions and the tape thickness direction which is orthogonal to the X and Y directions is expressed as the Z direction (the same applies below).

Figure 1:
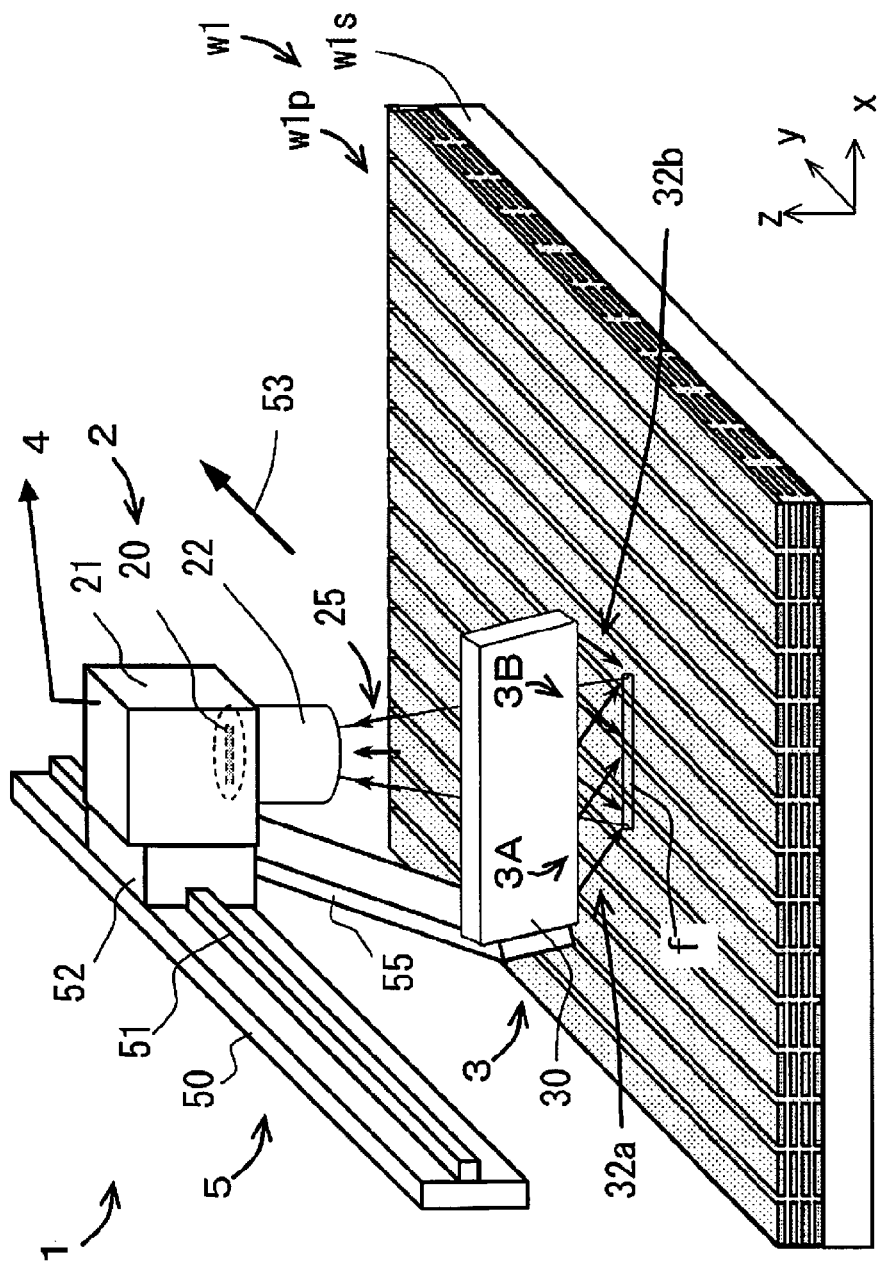
FIG. 1 is a perspective diagram illustrating an outline configuration of a checking apparatus according to the present invention.

FIG. 1 is a perspective diagram illustrating an outline configuration of a checking apparatus according to the present invention and is an example of one aspect for checking a structural object (referred to below as a checking target object) w1 which is a checking target with a flat plate shape. The checking target object w1 is laminated with many layers with fiber reinforced plastic tape w1p on the surface of a structural object w1s with changes in direction.

A checking apparatus 1 is configured to be provided with an imaging section 2, an illuminating section 3, a checking section 4, and a moving section 5. The checking apparatus 1 is an apparatus for checking the adherence state of the fiber reinforced plastic tape w1p which is adhered by a plurality being lined up on the surface of the checking target object w1.

The imaging section 2 images reflected light from an imaging region f with a line shape which is set on the fiber reinforced plastic tape w1p which is adhered by a plurality being lined up on the surface of the structural object w1s. Here, reflected light referred to here is not limited to regular reflection components of light and includes light with so-called scatter components, and light which is imaged by the imaging section 2 out of the reflected light is referred to as imaging light.

The imaging section 2 is configured to include an imaging camera 21 and a lens 22.

The imaging camera 21 is provided with a line sensor 20. The line sensor 20 is configured by a plurality of light detection elements being aligned in a direction which intersects with the relative movement direction.

The imaging camera 21 outputs a signal to the outside using a designated scanning rate to correspond with light which is received by the line sensor 20.

Although described later in detail, the illuminating section 3 radiates illumination light toward the imaging region f. Furthermore, the illuminating section 3 is provided with a first illuminating group 3A and a second illuminating group 3B.

Although described later in detail, the checking section 4 checks the adherence state of the fiber reinforced plastic tape based on an image which is imaged by the imaging section 2.

The relative moving section 5 relatively moves the imaging section 2 and the illuminating section 3 with regard to the fiber reinforced plastic tape which is adhered by a plurality being lined up on the surface of the structural object.

In detail, it is possible for an aspect as follows to be given as an example of the relative moving section 5.

1) The imaging section 2 and the illuminating section 3 are arranged on a Y axis slider mechanism so as to move in the longitudinal direction (that is, the Y direction) of the fiber reinforced plastic tape while the checking target object w1 with a flat plate shape is fixed. The Y slider mechanism which is given as an example here has the meaning of a mechanism where a rail 51 which extends in a straight line in the Y direction is arranged on a base 50 and where it is possible for a moving body which is referred to as a slider 52 to be moved to a designated position on the rail 51 or be stationary using the slider 52 and a motor and a ball screw or a linear motor (the same applies to below).

2) The checking target object w1 with a flat plate shape is arranged on a slider mechanism so as to be moved in the Y direction in a state where the imaging section 2 and the illuminating section 3 are fixed.

It is possible for a plurality of strips of the fiber reinforced plastic tape w1p with a designated width to be imaged by the imaging camera 21 scanning and moving in a direction which is indicated by an arrow 53 since the relative moving section 5 is configured as described above.

[Detailed Description of Illuminating Section]

Figure 2:
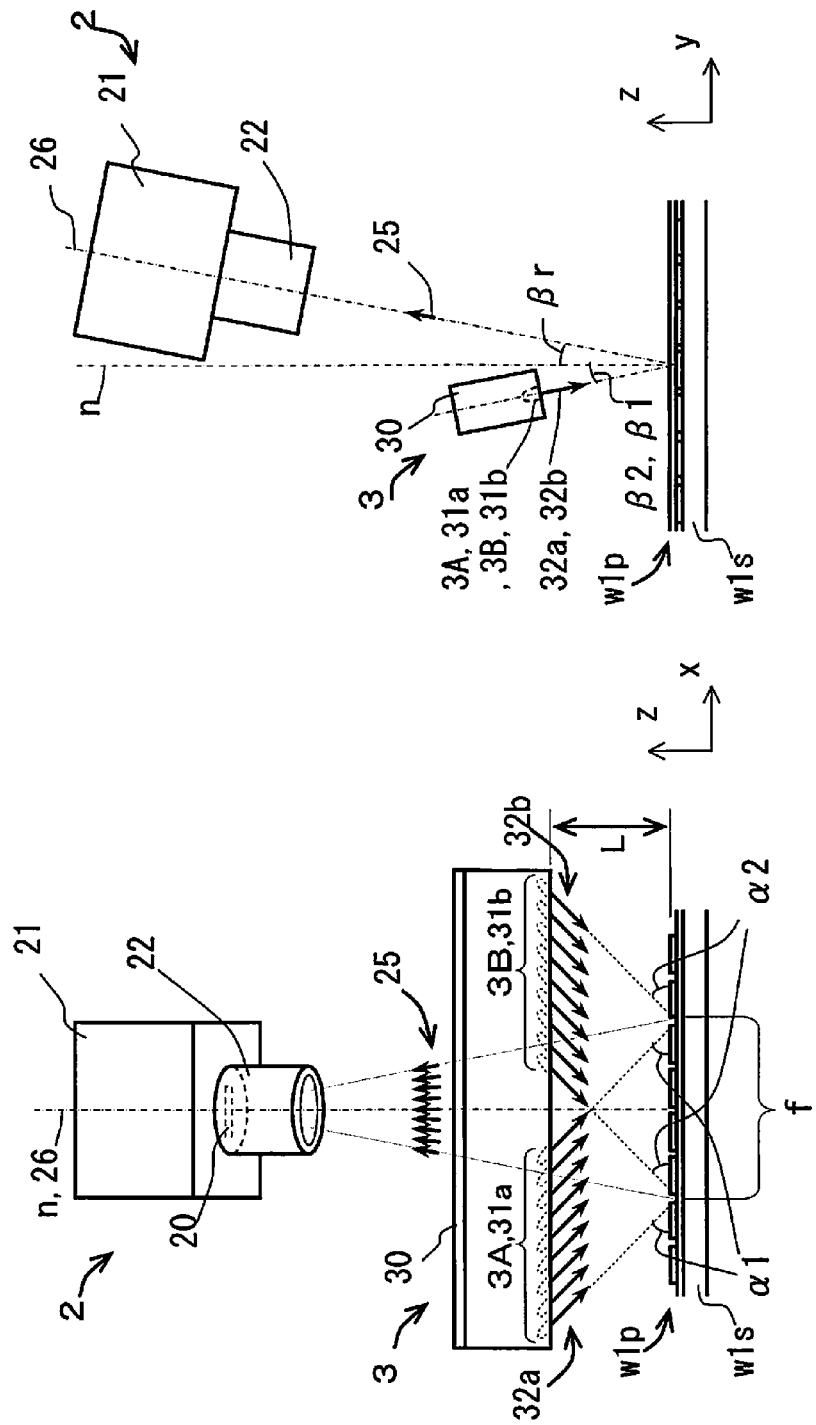
FIGS. 2A and 2B are diagrams illustrating the arrangement of an illuminating section and an imaging section in the checking apparatus according to the present invention.

FIGS. 2A and 2B are diagrams illustrating the arrangement of the illuminating section and the imaging section in the checking apparatus according to the present invention.

FIG. 2A illustrates an appearance of the imaging section 2 and the illuminating section 3 of the checking apparatus 1 which is shown in FIG. 1 viewed from the Y direction.

FIG. 2B illustrates an appearance of the imaging section 2 and the illuminating section 3 of the checking apparatus 1 which is shown in FIG. 1 viewed from the X direction.

The fiber reinforced plastic tape w1p which is the checking target is aligned so that a direction in which the fibers extend matches with the Y direction in a state where the fiber reinforced plastic tape w1p is lined up in the X direction. In this case, the imaging camera 2 is arranged so that the longitudinal direction of the line sensor 20 is a direction which intersects with the direction in which the fibers of the fiber reinforced plastic tape w1p extend, and more preferably, in a direction (that is, the X direction) which is orthogonal with the direction in which the fibers of the fiber reinforced plastic tape w1p extend.

Furthermore, the illuminating section 3 is configured so as to be arranged so that the light which is radiated from the first illuminating group 3A and the second illuminating group 3B uniformly irradiates light with a designated angle from a designated direction with regard to the illumination light radiating region which is wider than the imaging region f.

In more detail, the first illuminating group 3A is provided with a plurality of light emitting sections 31a which are arranged to line up in a direction which intersects with the fiber direction of the fiber reinforced plastic tape, and more preferably, in a direction (that is, the X direction) which is orthogonal with the fiber direction of the fiber reinforced plastic tape. Then, the first illuminating group 3A is such that main optical axes of the illumination light beams which are radiated from each of the light emitting sections 31a is set at a designated inclination angle $\alpha 1$ viewed from the fiber direction of the fiber reinforced plastic tape (that is, the Y direction) with regard to the surface of the imaging region f. Furthermore, each of the light emitting sections 31a of the first illuminating group 3A are such that the distances on the main optical axes between the surface of the fiber reinforced plastic tape w1p and each of the light emitting sections are set to be the same. Here, the main optical axis of the illumination light beam has the meaning of an optical axis of a portion where the light emission intensity is the highest among the light fluxes which are emitted from the light emitting sections (the same applies below).

In addition, the second illuminating group 3B is provided with a plurality of light emitting sections 31b which are arranged to line up in a direction which intersects with the fiber direction of the fiber reinforced plastic tape, and more preferably, in a direction (that is, the X direction) which is orthogonal with the fiber direction of the fiber reinforced plastic tape. Then, the second illuminating group 3B is such that main optical axes of the illumination light beams which are radiated from each of the light emitting sections 31b are set at a designated inclination angle $\alpha 2$, which is different to the first illuminating group 3A, viewed from the fiber direction of the fiber reinforced plastic tape (that is, the Y direction) with regard to the surface of the imaging region f.

Furthermore, each of the light emitting sections 31b of the second illuminating group 3B are such that the distances on the main optical axes between the surface of the fiber reinforced plastic tape w1p and each of the light emitting sections are set to be the same.

Each of the light emitting sections 31a in the first illuminating group 3A are such that apparent intervals L between each of the light emitting sections 31a and the checking target surface are parallel if the inclination angle α1 of the main optical axis of the illumination light beams are the same viewed from the Y direction. By doing this, the distances on the main optical axes are the same. The same applies to each of the light emitting sections 31b in the second illuminating group 3B.

In addition, although described later in detail, there may be an aspect where the inclination angle of the main optical axis of the illumination light beams viewed from the Y direction are all different, and due to this, apparent intervals between the light emitting sections and the checking target surface are all different. In this case, the same applies to each of the light emitting sections of the second illuminating group 3B.

Here, although the plurality of light emitting sections which are used in the first illuminating group 3A and the second illuminating group 3B will be described in more detail later, it is possible to give an example of an aspect of a combination of LED illumination or halogen illumination and optical fibers.

In addition, the illuminating section 3 is such that main optical axes 32a of the illumination light beams which radiate from each of the light emitting sections 31a of the first illuminating group 3A are arranged with a designated inclination angle β1 with regard to a normal line n of the imaging region f seen from the X direction. In the same manner, main optical axes 32b of the illumination light beams which radiate from each of the light emitting sections 31b of the second illuminating group 3B are arranged with a designated inclination angle β2 with regard to the normal line n of the imaging region f seen from the X direction. The inclination angle β2 may be set to be the same as the inclination angle β1 if there is an aspect where each of the light emitting sections 31b of the second illuminating group 3B are lined up on a straight line with each of the light emitting sections 31a of the first illuminating group 3A.

In addition, the imaging camera 21 of the imaging section 2 is such that an imaging optical axis 26 may be arranged to match the normal line n of the imaging region for may be arranged to be inclined at a designated angle βr with the normal line n of the imaging region f seen from the X direction. The imaging optical axis 26 is set so that a casing 30 for the illuminating section 3 has a positional relationship so as not to block the imaging optical axis 26 or is set to a positional relationship so that the contrast of an image which is imaged as described below (that is, the difference between the signal intensities of white images and black images) is larger.

[Detailed Description of Checking Section]

Figure 3:
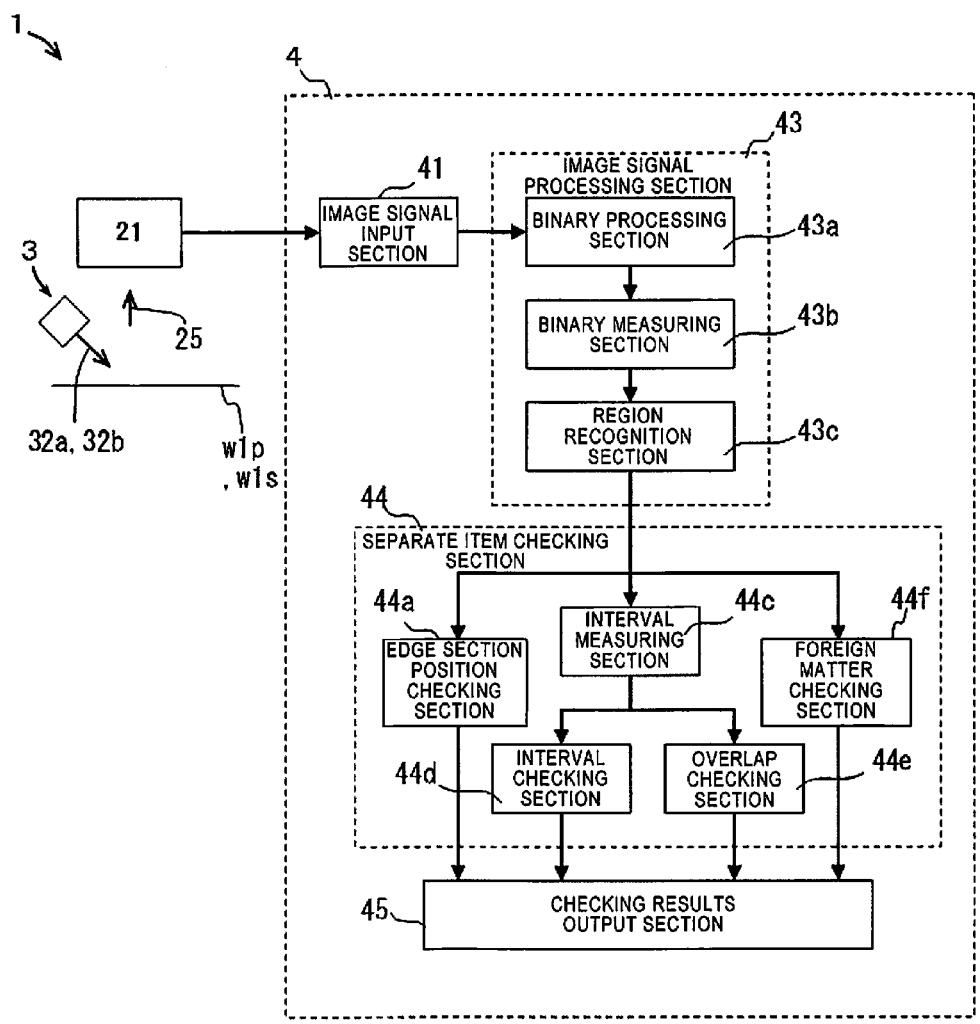
FIG. 3 is a block diagram of the checking apparatus according to the present invention.

FIG. 3 is a block diagram of the checking apparatus according to the present invention and illustrates the details of each section which configures the checking apparatus 1. The checking section 4 is provided with an image signal input section 41, an image signal processing section 43, a separate item checking section 44, and a checking results output section 45. In detail, it is possible for the checking section 4 to use an image processing apparatus which is generally available, and the details of each section will be described below.

The image signal input section 41 is for inputting signals which are output from the imaging camera 21.

The image signal processing section 43 outputs data by quantifying the levels and intervals between the fiber reinforced plastic tape w1p in accordance with a sequence where there is prior programming of signals which are input from the image signal input section 41.

The separate item checking section 44 performs checking of separate items by comparing a checking reference which is stipulated in advance with regard to data which is output from the image signal processing section 43.

The checking results output section 45 outputs the results where the separate items are checked.

The image signal processing section 43 is provided with a binary processing section 43a, a binary measuring section 43b, and a region recognition section 43c.

The binary processing section 43a extracts a tape portion, which appears bright, as a white image and a tape layer, which is a lower layer which appears dark, as a black image by binarizing the image data which is obtained by the image signal input section 41. The binary measuring section 43b computes by calculating the area, width, length, direction, and the like for each cluster which is a white portion with regard to image data which is binarized into white and black using the binary processing section 43a.

The region recognition section 43c recognizes clusters, which enter into a designated range for area, width, length and direction, among the clusters which are white portions as a tape portion and recognizes a region where there is a tape portion as a checking target region. The region recognition section 43c performs, for example, a bounding rectangle fitting process with regard to each of the ranges which are recognized as tape portions. The bounding rectangle fitting process performs a fitting process based on least squares method so that the rectangles are bound and computes positional coordinates for each of the edge sections in the X and Y direction with regard to the clusters which are white portions which are recognized as tape portions.

In detail, the image signal processing section 43 is configured by combining the hardware of an image processing apparatus and an execution program (software) for realizing each function of the binary processing section 43a, the binary measuring section 43b, and the region recognition section 43c which are described above.

The separate item checking section 44 has an edge section position checking section 44a, an interval measuring section 44c, an interval checking section 44d, an overlap checking section 44e, and a foreign matter checking section 44f.

Figure 4A:
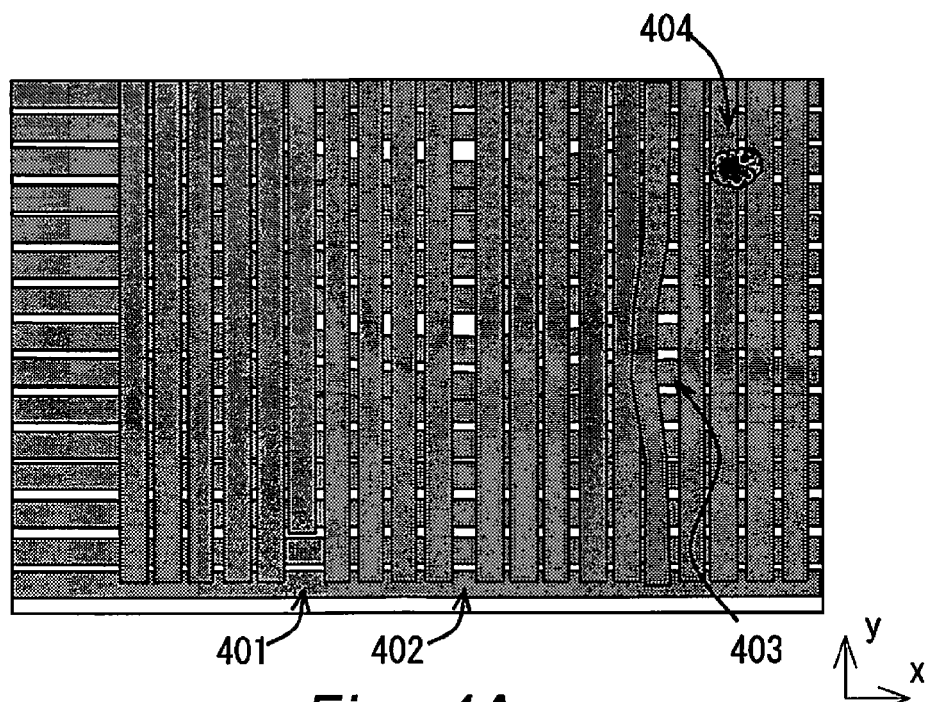
FIGS. 4A and 4B are diagrams illustrating a state where a checking target object is imaged using the checking apparatus according to the present invention.
Figure 4B:
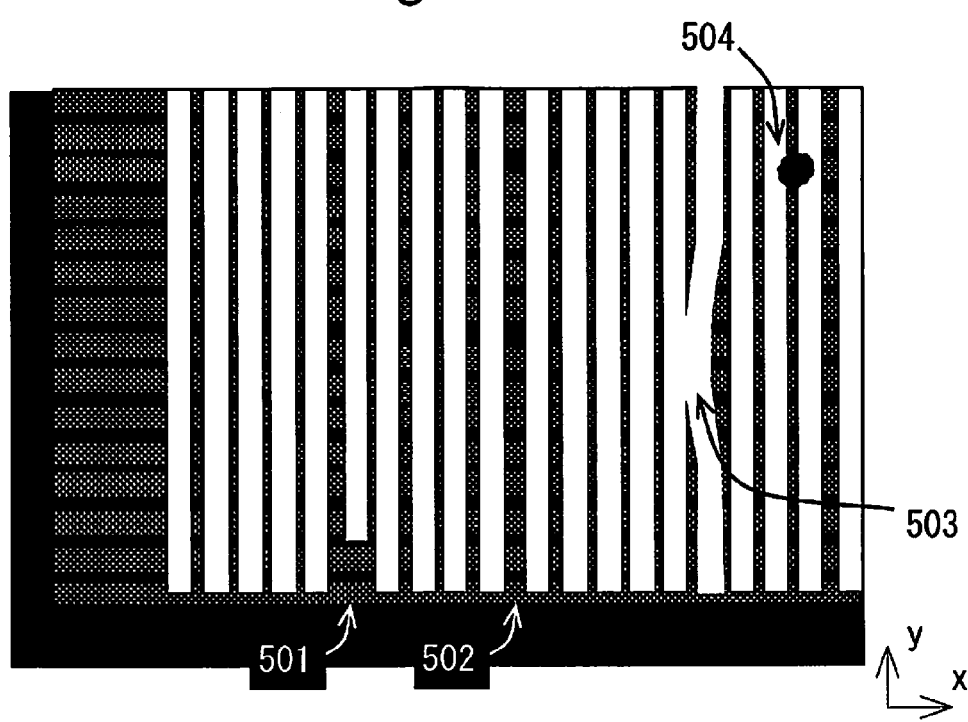

FIGS. 4A and 4B are diagrams illustrating a state where the checking target object is imaged using the checking apparatus according to the present invention, FIG. 4A is a diagram illustrating the outer appearance of the checking target object w1 inside the imaging region f, and FIG. 4B is an image diagram illustrating an imaged image.

An appearance, where there are the errors as described below with regard to the checking target object w1, is expressed in FIG. 4A.

1) There is an error which is referred to as an "edge section mismatch" at a portion which is indicated by an arrow 401 where the position of the edge section of a strip of tape is deviated in the Y direction relative to the edge section of another strip of tape.

2) There is an error which is referred to as a "gap abnormality" at a portion which is indicated by an arrow 402 since the interval in the X direction between strips of tape which are adjacent is wider than the stipulated value.

3) There is an error which is referred to as an "overlap abnormality" at a portion which is indicated by an arrow 403 where strips of tape which are adjacent overlap.

4) There is an error which is referred to as a "foreign matter adherence" at a portion which is indicated by an arrow 404 where a foreign matter is adhered on the surface of the tape.

A state is expressed in FIG. 4B where a region which corresponds to FIG. 4A is imaged using the imaging camera 21 due to being moved and scanned and is output as a white and black image due to the binary processing.

The tape which is shown in FIGS. 4A and 4B is adhered in a state where each of the fibers extends in the Y direction, and the tape portion which is the uppermost layer is imaged as white (as a bright section) and the tape which is in the lower layers is imaged as black (as a dark section) when the checking target object w1 is imaged as an application of the present invention. For this reason, the portion, where the tape which forms the layer which is the checking target is adhered, is displayed as white and a portion where there are various errors described above is displayed in the following manner.

1) The boundary of the white portion and the black portion is deviated at a location where there is an edge section mismatch error which is shown by an arrow 501.

2) The interval between the black portions is wide at a location where there is a gap abnormality error which is shown by an arrow 502.

3) There is no black portion or the interval between the white portions is close to double the designated width at a location where there is an overlap abnormality error which is shown by an arrow 503.

4) A black region enters into a region which is to be white at a location where there is a foreign matter adherence error which is shown by an arrow 504.

Detection is performed with regard to these errors by each of the checking sections in the separate item checking section 44 described above.

The edge section position checking section 44*a* approximates the positional coordinates of the edge section in the Y direction as linear for each of the tape portions which are calculated by the region recognition section 43*c* and determines that the tape portion is an "error" if the bounding rectangle for the edge section position is outside of a stipulated range. Due to this, it is possible to detect edge section mismatch errors.

The interval measuring section 44*c* measures the position of the edge section in the X direction for each of the tape portions which are calculated by the region recognition section 43*c* and measures the width of the gaps between each of the tape portions (that is, the X direction for the black portions). The interval checking section 44*d* determines that the widths of the black portions are "OK" if within the range of stipulated values and determines that there is an "error" in the widths of the black portions if outside of the range of stipulated values. Due to this, it is possible to detect gap abnormality errors. The overlap checking section 44*e* determines that the widths of the white portions are "OK" if within the range of stipulated values and determines that there is an "error" in the widths of the white portions if outside of the range of stipulated values. Due to this, it is possible to detect overlap abnormality errors.

The foreign matter checking section 44*f* measures the area of a black portion which exists within a region which is a white portion which is approximated as being rectangular using the region recognition section 43*c*, determines that the black portion is "OK" if the black portion is not a designated area or larger, and determines that the black portion is an "error" if the black portion is a designated area or larger. Due to this, it is possible to detect foreign matter adherence errors.

In detail, the separate item checking section 44 is configured by combining the hardware of an image processing apparatus and an execution program (software) for realizing each function of the edge section position checking section 44*a*, the interval measuring section 44*c*, the interval checking section 44*d*, the overlap checking section 44*e*, and the foreign matter checking section 44*f* described above.

The checking results output section 45 outputs the errors which are detected by the separate item checking section 44 to the outside. In detail, it is possible for a signal output section or a data transmitting section which is provided in an image processing apparatus or a signal output unit or a data transmitting unit which is connected to an image processing apparatus to be given as examples of the checking results output section 45.

Then, imaging is performed while the location of the imaging region f, which is set on the fiber reinforced plastic tape w1*p*, is deviated by moving the relative moving section 5. By doing this, it is possible to perform checking of the adherence state of a plurality of strips of the fiber reinforced plastic tape w1*p* while relatively moving the imaging section 2 in the adherence direction of the fiber reinforced plastic tape w1*p*.

In addition, the relative moving section 5 is configured so that it is also possible to relative move the imaging section 2 and the checking target object in the X direction in a case where checking is performed over a wider range in the longitudinal direction of the imaging region f using the imaging section 2. For example, a rail which extends in the X direction is arranged in the relative moving section 5, and an X axis slider mechanism (which is not shown in the diagrams) which is provided with a slider which moves itself or is stationary on the rail is provided along with the rail.

Then, the checking apparatus is configured by combinations as described below being realized.

1) The imaging section 2 and the illuminating section 3 are placed on the slider 52 which is a Y axis slider mechanism and the base 50 of the Y axis slider mechanism is placed on the slider which is an X axis slider mechanism.

2) The checking target object is placed on the slider which is an X axis slider mechanism.

A series of actions, where checking is performed for each of the imaging regions, is carried out using the relative moving section 5 as described above and checking is performed with regard to the whole surface of the checking target object w1. It is possible to perform automatic checking with regard to the whole surface of the checking target object w1 when using the checking apparatus 1 which is provided with this configuration.

It is possible to appropriately perform checking with regard to the adherence state of the fiber reinforced plastic tape which is formed on the uppermost layer since the checking apparatus 1 according to the present invention is configured as described above. That is, checking is performed by focusing on the adherence state of the uppermost layer of tape with any effects from the fiber direction of the lower layer since the illumination light is selected and radiated from a direction which is suitable for the fiber direction of the fiber reinforced plastic tape. Furthermore, it is possible to obtain the same checking results even when the imaging positions within the imaging region f with a line shape differ (that is, irrespective of a central portion or a peripheral portion) and there is an effect that swift checking is possible with regard to the adherence state of the fiber reinforced plastic tape which is adhered by a plurality being lined up on the surface of a structural object.

[Detailed Configuration of Illuminating Section]

Figure 5:
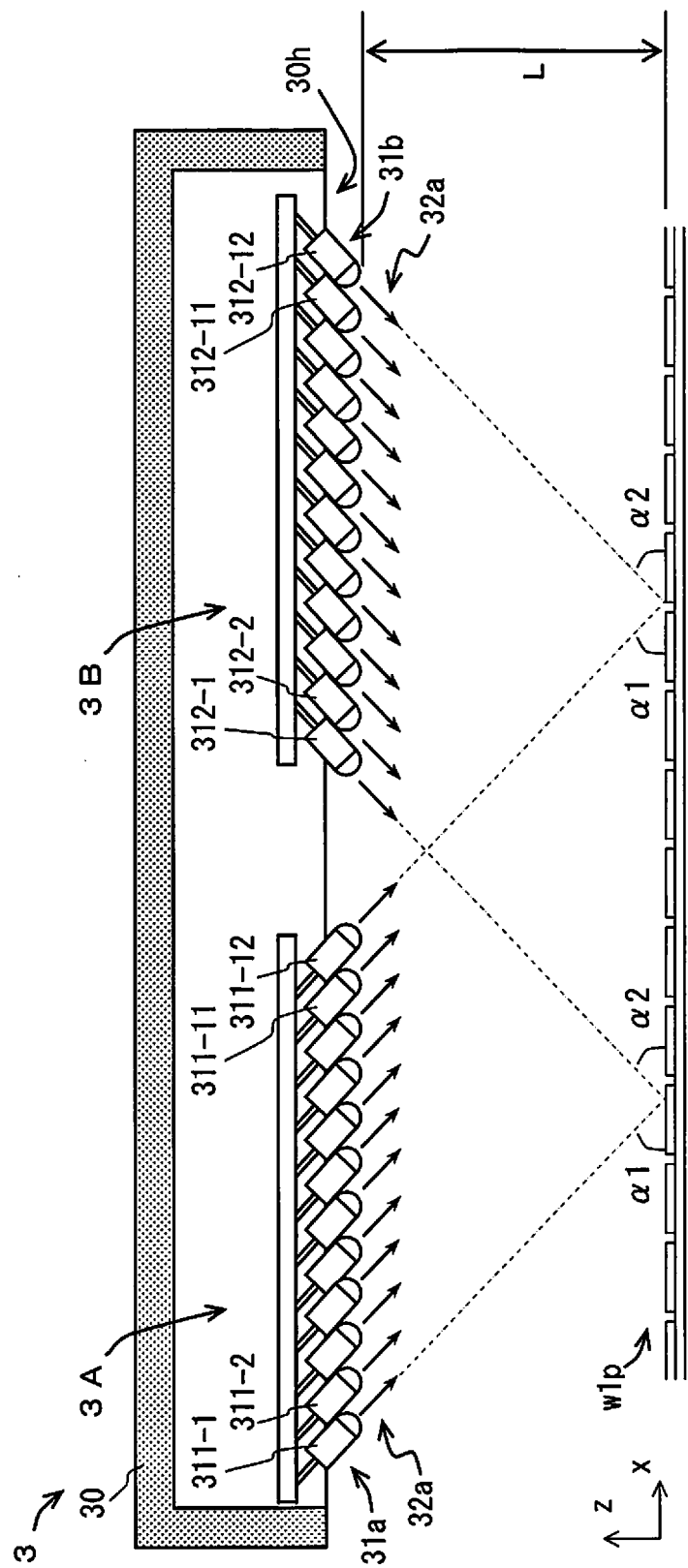
FIG. 5 is a cross sectional diagram of an aspect of an illuminating section according to the present invention.

FIG. 5 is a cross sectional diagram of an aspect of the illuminating section according to the present invention and expresses an internal configuration of the illuminating section 3 which is shown in FIGS. 2A and 2B.

The casing 30 of the illuminating section 3 is configured in a box shape and an opening section 30h is provided in the lower surface side (the lower side in the paper surface in FIG. 5). Furthermore, the light emitting sections 31a where a plurality of light emitting diodes (311-1, 311-2, . . . , 311-11, 311-12) are arranged to line up with designated intervals and the light emitting section 31b where a plurality of light emitting diodes (312-1, 312-2, . . . , 312-11, 312-12) are arranged to line up with designated intervals are provided inside the casing 30. Each of the light emitting diodes (311-1, 311-2, . . . , 311-11, 311-12) which configure the light emitting section 31a are arranged so that the main optical axes 32a of the light which is radiated from the light emitting diodes are parallel and configures the first illuminating group 3A. In the same manner, each of the light emitting diodes (312-1, 312-2, . . . , 312-11, 312-12) which configure the light emitting section 31b are arranged so that the main optical axes 32b of the light which is radiated from the light emitting diodes are parallel and configures the second illuminating group 3B.

Figure 6:
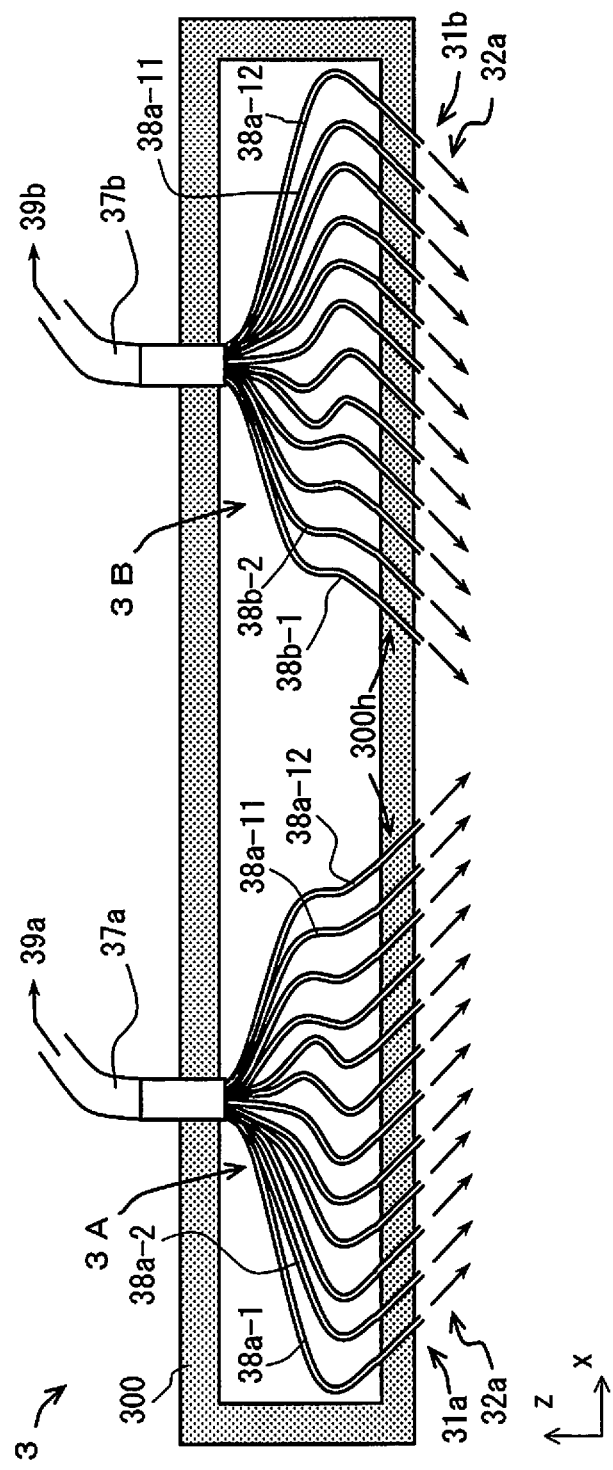
FIG. 6 is a cross sectional diagram of another aspect of an illuminating section according to the present invention.

FIG. 6 is a cross sectional diagram of another aspect of an illuminating section according to the present invention and expresses an internal configuration of an aspect which is different to the illuminating section 3 which is shown in FIG. 5.

A casing 300 of the illuminating section 3 is configured in a box shape, two opening sections are provided in the upper surface of the box shape, and a plurality of opening sections are provided in the lower surface of the box shape with designated intervals. Bunched optical fibers 37a and 37b are attached in two of the opening sections at the upper surface of the box shape.

The bunched optical fibers 37a and 37b are branched inside the casing 300.

Edge sections 39a and 39b of the bunched optical fibers 37a and 37b are connected to an illumination light source unit (which is not shown in the diagrams) and are configured so that light which is radiated from the illumination light source is introduced and illumination light is radiated from each of the one edge sides of branched optical fibers 38a-1 to 38a-12 and 38b-1 to 38b-12.

The one edge sides of the branched optical fibers 38a-1 to 38a-12 are connected to the plurality of opening section which are each provided in the lower surface of the box shape with designated intervals. Then, the one edge sides of the branched optical fibers 38a-1 to 38a-12 configure the light emitting section 31a (that is, the first illuminating group 3A) by being arranged so as to line up so that it is possible for light to be radiated in a state of protruding by only designated dimensions from the lower surface side of the box shape of the casing 300 by passing through the plurality of openings.

In the same manner, the one edge sides of the branched optical fibers 38b-1 to 38b-12 are connected to the plurality of opening section which are provided on the lower surface of the box shape with designated intervals. Then, the one edge sides of the branched optical fibers 38a-1 to 38a-12 configure the light emitting section 31b (that is, the second illuminating group 3B) by being arranged so as to line up so that it is possible for light to be radiated in a state of protruding by only designated dimensions from the lower surface side of the box shape of the casing 300 by passing through the plurality of openings.

[Another Embodiment]

On top of realizing the present invention, it is possible to use the lens 22 of the imaging section 2 provided with a plurality of combinations of convex lenses and concave lenses and it is possible for CCTV or telecentric lenses or object lenses such as in optical microscopes which are generally available to be given as examples of the lens 22. By doing this, it is possible to obtain a sharp image with high contrast with checking of the adherence state of the fiber reinforced plastic tape since illumination light radiates from a direction which intersects with a direction in which the fibers of the fiber reinforced plastic tape extend.

Here, using a telecentric focusing optical lens as the lens 22 of the imaging section 2 is more preferable. By doing this, the light quantity difference is extremely small between the center and the periphery section of the imaging region f with a line shape and it is possible to obtain the same checking results even when the imaging positions within the imaging region f with a line shape differ.

[Another Embodiment]

On the other hand, it is more preferable to realize the illuminating section 3 with the following configuration in a case where a non-telecentric focusing optical lens is used.

Figure 7:
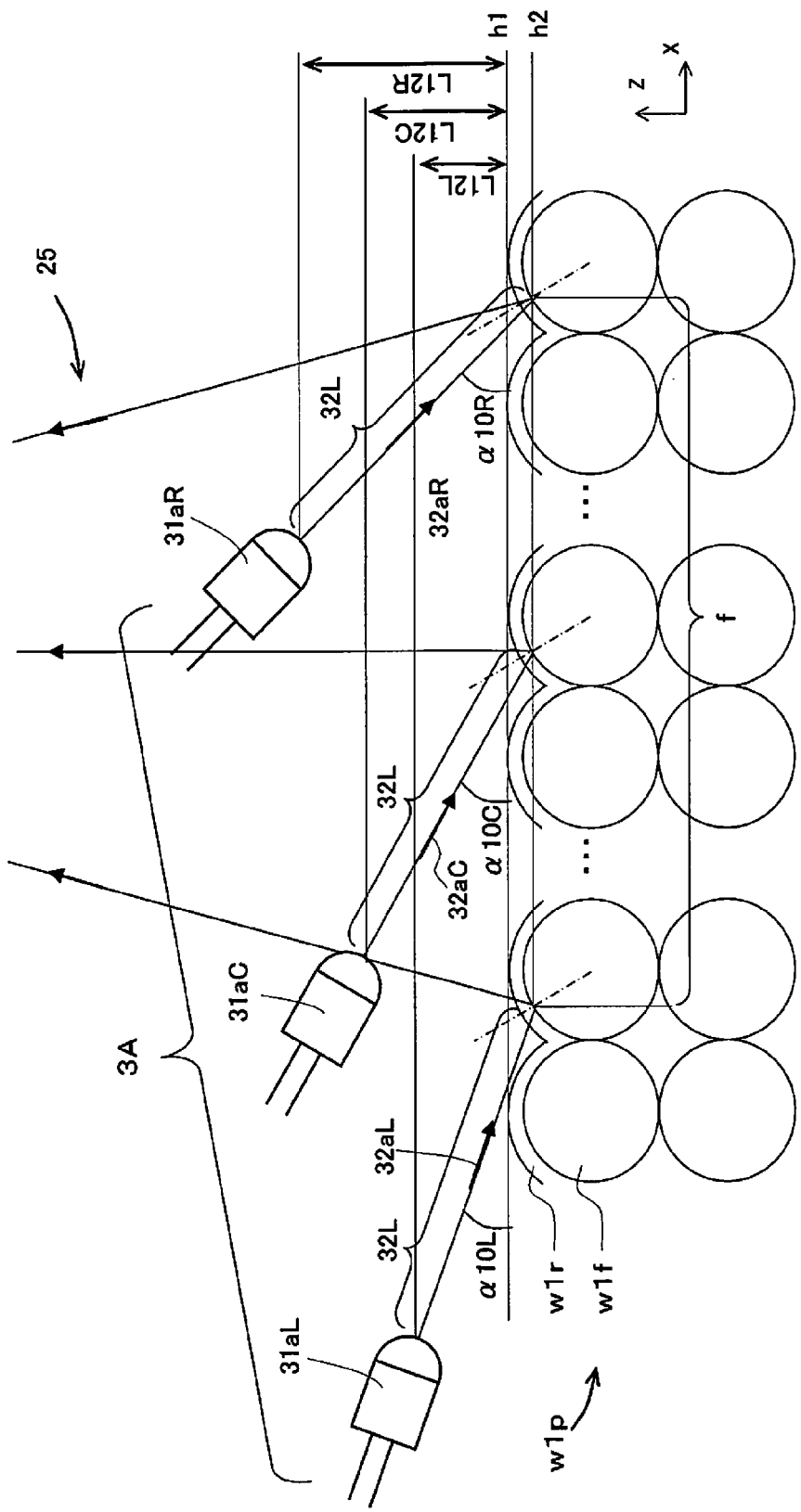
FIG. 7 is a diagram illustrating a detailed configuration of yet another aspect of an illuminating section according to the present invention.

FIG. 7 is a diagram illustrating a detailed configuration of yet another aspect of an illuminating section according to the present invention. Cross sections of a plurality of fibers w1f which configure the fiber reinforced plastic tape w1p and resin w1r which bonds the fibers w1f are shown in FIG. 7. In addition, in FIG. 7, light which is radiated from the first illuminating group 3A is reflected by the surface of the fibers w1f and observation light with a direction which is shown by an arrow 25 is imaged using the line sensor 20. Here, a light emitting section 31aR which is on the right edge, a light emitting section 31aC which is in the center, and a light emitting section 31aL which is on the left edge out of each of the light emitting sections which configure the first illuminating group 3A viewed from the Y direction are shown in the diagram in FIG. 7 and the other light emitting section are omitted in order to simplify the description.

In this aspect, distances 32R, 32C and 32L on main optical axis 32aR, 32aC, and 32aL from each of the light emitting sections 31aR, 31aC, and 31aL to the fiber reinforced plastic tape w1p are all the same with regard to the imaging region f, but inclination angles $\alpha 10R$, $\alpha 10C$, and $\alpha 10L$ of the main optical axis of each of the light emitting sections are all different with regard to the imaging region f. For this reason, apparent distances L12R, L12C, and L12L from each of the light emitting sections 31aR, 31aC, and 31aL to the fiber reinforced plastic tape w1p are all the different.

At this time, the inclination angles $\alpha 10R$, $\alpha 10C$, and $\alpha 10L$ are set as angles where the inclination angles with the main optical axes of each of the light emitting sections are all different in consideration of the imaging optical axis 26 with regard to each position of the imaging region f based on the angle of view of the lens 22 and the position of the imaging region f. Then, the inclination angles are set so that the reflection peaks of the illumination light beams are the same for each of the fibers w1f in the fiber reinforced plastic tape w1p during imaging using the imaging section. That is, the apparent surface of the fiber reinforced plastic tape w1p are positions which are indicated as h1 and the reflection peaks of the illumination light beams for each of the fibers w1f are positions which are indicated as h2.

Here, in this aspect, each of the illumination sections 31b which configure the second illuminating group 3B are arranged in the same manner so that the inclination angles of the main optical axes are all different.

According to the description above, it is possible for changes in the light quantity at the center and the peripheral sections of the imaging regions f to be extremely small even in a case where a non-telecentric focusing optical lens is used.

[Another Embodiment]

It is possible for the adherence state of the fiber reinforced plastic tape to be checked using the checking apparatus 1 with the configuration described above, but it is also possible to perform checking using checking apparatuses 1b and 1c which are other embodiments.

Figure 8B:
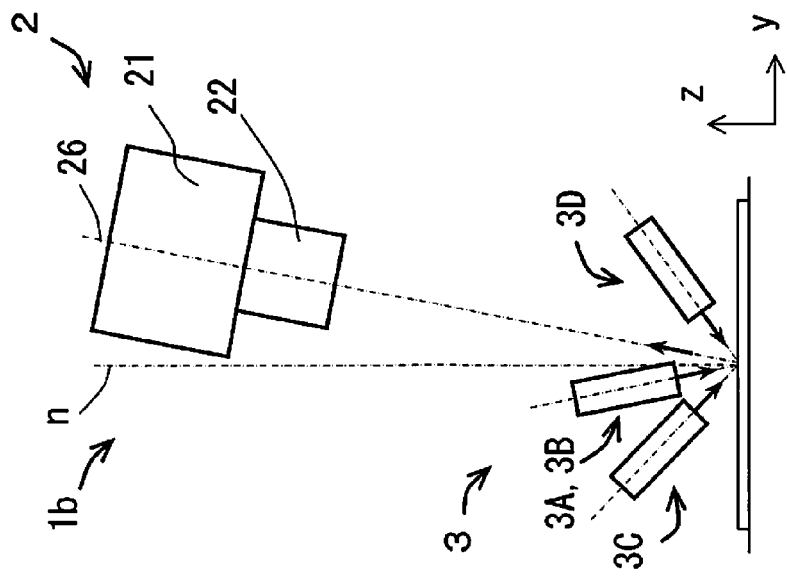
FIGS. 8A and 8B are diagrams illustrating a detailed configuration of yet another aspect of an illuminating section according to the present invention.
Figure 8A:
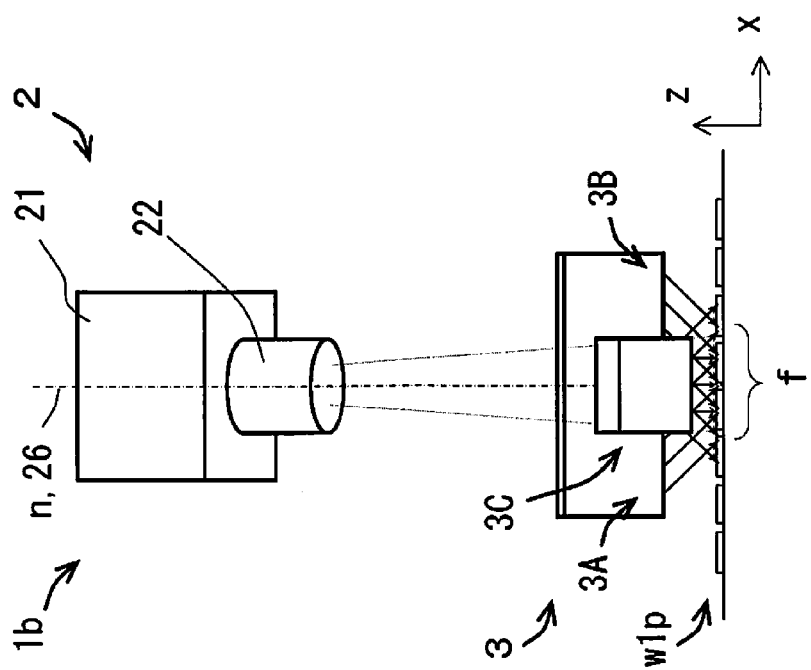

FIGS. 8A and 8B are diagrams illustrating a detailed configuration of yet another aspect of an illuminating section according to the present invention. FIG. 8A is a diagram of the imaging section 2 and the illuminating section 3 which configure the checking apparatus 1b viewed from the Y direction, and FIG. 8B is a diagram of the imaging section 2 and the illuminating section 3 which configure the checking apparatus 1b viewed from the X direction.

The checking apparatus 1b is configured by being provided with a third illuminating group 3C and a fourth illuminating group 3D in the illuminating section 3 in addition to the configuration of the checking apparatus 1 described above.

Each of the light emitting sections which configure the third illuminating group 3C are arranged so as to line up in one row in the X direction and are arranged so that illumination light is radiated in parallel with regard to the imaging region f in the same manner as the first illuminating group 3A and the second illuminating group 3B. In the same manner, each of the light emitting sections which configure the fourth illuminating group 3D are arranged so as to line up in one row in the X direction and are arranged so that illumination light is radiated in parallel with regard to the imaging region f.

In the case of this aspect, there is a configuration where the first illuminating group 3A and the second illuminating group 3B are turned on simultaneously and scanning and imaging for checking is performed. During this, the third illuminating group 3C and the fourth illuminating group 3D are turned off. Then, checking is performed in a state where the fiber reinforced plastic tape w1p is adhered to line up in the X direction (the fibers extend in the Y direction) by performing scanning and imaging in the same manner as the checking apparatus 1 described above.

On the other hand, there is a configuration where the third illuminating group 3C and the fourth illuminating group 3D are turned on simultaneously and scanning and imaging for checking is performed. During this, the first illuminating group 3A and the second illuminating group 3B are turned off. Then, scanning and imaging is performed by relatively moving the imaging section 2 and the illuminating section 3 in the Y direction in the same manner as the checking apparatus 1 described above and images are compounded after this. By doing this, checking is swiftly performed by scanning and imaging only in the Y direction even with a state where the fiber reinforced plastic tape w1p is adhered to line up in the Y direction (the fibers extend in the X direction). Moreover, it is possible to obtain the same checking results even when the positions within the field of view for imaging differ.

Figure 9A:
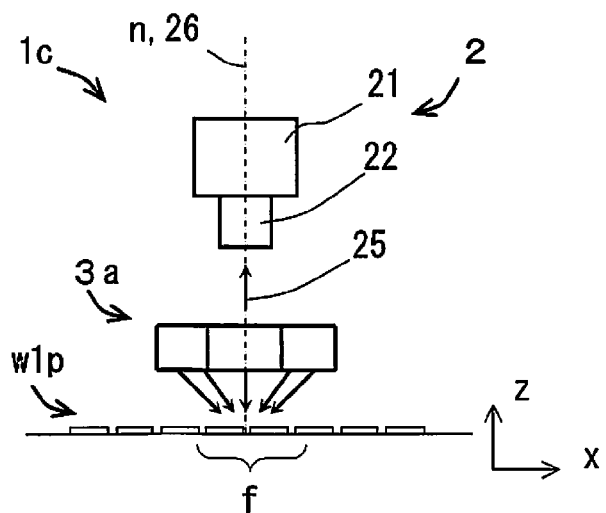
FIGS. 9A and 9B are diagrams illustrating a detailed configuration of yet another aspect of an illuminating section according to the present invention.
Figure 9B:
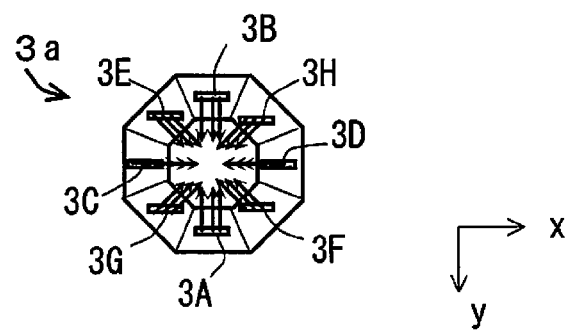
Figure 10:
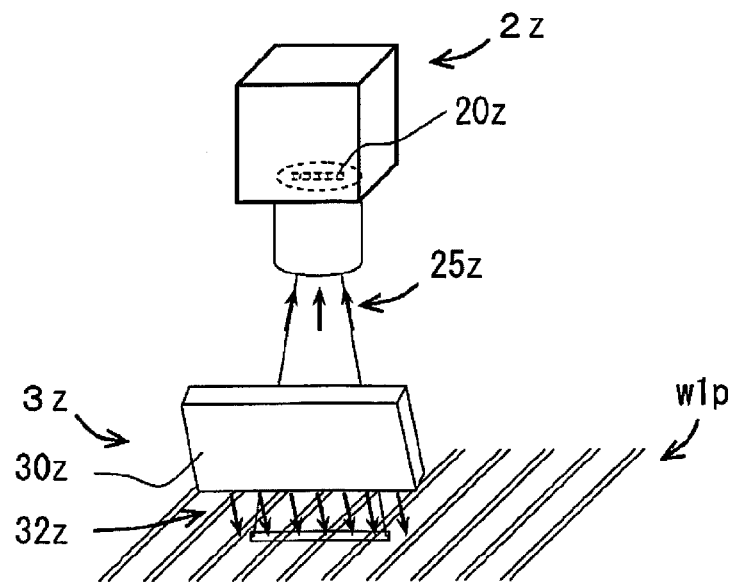
FIG. 10 is a diagram illustrating the arrangement of an illuminating section and an imaging section in a checking apparatus in the prior art.

FIGS. 9A and 9B are diagrams illustrating a detailed configuration of yet another aspect of an illuminating section according to the present invention. FIG. 9A is a diagram of the imaging section 2 and an illuminating section 3a which configure the checking apparatus 1c viewed from the Y direction, and FIG. 9B is a diagram of the illuminating section 3a which configures the checking apparatus 1c viewed from the Z direction (that is, a diagram viewed from below).

The checking apparatus 1c is configured to be provided with the illuminating section 3a which is another aspect while the configuration of the checking apparatus 1b described above is the base. The illuminating section 3a is configured to be provided with a first illuminating group 3A to an eighth illuminating section 3H. In addition, the first illuminating group 3A and the second illuminating group 3B are a pair, the third illuminating section 3C and the fourth illuminating section 3D are a pair, the fifth illuminating section 3E and the sixth illuminating section 3F are a pair, and the seventh illuminating section 3G and the eighth illuminating group 3H are a pair, and the imaging optical axis 26 of the imaging section 2 is arranged so as to be surrounded. Each of the light emitting sections which configure the first illuminating group 3A to the eighth illuminating group 3H are arranged so as to line up in one row in the X direction in each of the illuminating groups as shown in FIG. 9B and are arranged so that the distances on the main axes of the illumination to the surface of the tape w1p are the same. In addition, there is a configuration where the first illuminating group 3A to the eighth illuminating group 3H are arranged by allocating in 45 degree units, the illuminating groups in each pair are turned on simultaneously and the other illuminating groups are turned off, and scanning and imaging for checking is performed. At this time, the illuminating groups in each pair are turned on so that the illumination light radiates from a direction which intersects with (preferably, a direction which is orthogonal to) the adherence direction of the fiber reinforced plastic tape w1p which is the uppermost layer.

According to the configuration of the checking apparatus 1c as above, it is possible to swiftly perform checking by scanning and imaging only in the Y direction not only in a state where the fiber reinforced plastic tape w1p, which is the uppermost layer which is the checking target, is adhered to line up in the X direction and the Y direction (the fibers extend in the Y direction and the X direction) but also even in a state where the fiber reinforced plastic tape w1p, which is the uppermost layer which is the checking target object, is adhered to line up in a diagonal direction therebetween if the imaging section 2 and the imaging section 3 scan and move by being relatively moved only in the Y direction. Moreover, it is possible to obtain the same checking results even when the positions in the view of field for imaging differ.

The invention claimed is:

1. An apparatus for checking an adherence state of a plurality of strips of fiber reinforced plastic tape that is adhered and lined up on a surface of a structural object, the apparatus comprising:
    an imaging section configured to image an imaging region with a line shape that is set on the fiber reinforced plastic tape;
    the imaging section has a line sensor in which a plurality of light detection elements are aligned in a direction that intersects with the relative movement direction;
    the imaging section further has a focusing optical element which includes a non-telecentric focusing optical element on at least the fiber reinforced plastic tape side of the focusing optical element;

an illuminating section configured to radiate illumination light toward the imaging region;

a checking section configured to check the adherence state of the fiber reinforced plastic tape based on an image that is imaged using the imaging section; and a moving section configured to move the illuminating section and the imaging section with respect to the fiber reinforced plastic tape that is adhered in a relative movement direction;

the illuminating section has a first illuminating group with a plurality of light emitting sections that are arranged to line up in a direction that intersects with a fiber direction of the fiber reinforced plastic tape;

the first illuminating group being configured such that main optical axes of illumination light beams that are radiated from each of the light emitting sections of the first illuminating group are set at a designated inclination angle with respect to a surface of the imaging region and distances on the main optical axes between the surface of the structural object and each of the light emitting sections of the first illuminating group are set to be the same;

the illuminating section further has a second illuminating group with a plurality of light emitting sections that are arranged to line up in a direction that intersects with the fiber direction of the fiber reinforced plastic tape;

the second illuminating group being configured such that main optical axes of illumination light beams that are radiated from each of the light emitting sections of the second illuminating group are set at an inclination angle that is different from the first illuminating group with respect to the surface of the imaging region and distances on the main optical axes between the surface of the structural object and each of the light emitting sections of the second illuminating group are set to be the same; and each of the light emitting sections in the first illuminating group and each of the light emitting sections in the second illuminating group are set at inclination angles such that reflection peaks of the illumination light beams are the same for each of fibers in the fiber reinforced plastic tape during imaging using the imaging section.

2. The apparatus for checking the adherence state of fiber reinforced plastic tape according to claim 1, wherein the illuminating section is configured such that illumination light beams radiate from an opening section that is provided in a part of a casing, the light emitting sections in the first illuminating group include light emitting diodes, respectively, that are arranged to line up in one row such that distances from the light emitting diodes to a checking region are equal in a state of being inclined with respect to a surface of the checking region, and the light emitting sections in the second illuminating group include light emitting diodes, respectively, that are arranged to line up in one row such that distances from the light emitting diodes to the checking region are equal in a state of being inclined with respect to the surface of the checking region.

3. The apparatus for checking the adherence state of fiber reinforced plastic tape according to claim 1, wherein the illuminating section is provided in a plurality of opening sections that are provided in a part of a casing, the light emitting sections in the first illuminating group and the light emitting sections in the second illumination are formed, respectively, by connecting one ends of branched optical fibers with the opening sections, the light emitting sections in the first illuminating group are arranged to line up in one row such that distances from the light emitting sections to a checking region are equal in a state of being inclined with respect to a surface of the checking region, and the light emitting sections in the second illuminating group are arranged to line up in one row such that distances from the light emitting sections to the checking region are equal in a state of being inclined with respect to the surface of the checking region.

4. The apparatus for checking the adherence state of fiber reinforced plastic tape according to claim 1, wherein the illuminating section is configured such that illumination light beams radiate from an opening section that is provided in a part of a casing, the light emitting sections in the first illuminating group include light emitting diodes, respectively, that are arranged to line up in one row such that distances from the light emitting diodes to a checking region are equal in a state of being inclined with respect to a surface of the checking region, and the light emitting sections in the second illuminating group include light emitting diodes, respectively, that are arranged to line up in one row such that distances from the light emitting diodes to the checking region are equal in a state of being inclined with respect to the surface of the checking region.

5. The apparatus for checking the adherence state of fiber reinforced plastic tape according to claim 1, wherein the illuminating section is configured such that illumination light beams radiate from an opening section that is provided in a part of a casing, the light emitting sections in the first illuminating group include light emitting diodes, respectively, that are arranged to line up in one row such that distances from the light emitting diodes to a checking region are equal in a state of being inclined with respect to a surface of the checking region, and the light emitting sections in the second illuminating group include light emitting diodes, respectively, that are arranged to line up in one row such that distances from the light emitting diodes to the checking region are equal in a state of being inclined with respect to the surface of the checking region.

6. The apparatus for checking the adherence state of fiber reinforced plastic tape according to claim 1, wherein the illuminating section is configured such that illumination light beams radiate from an opening section that is provided in a part of a casing, the light emitting sections in the first illuminating group include light emitting diodes, respectively, that are arranged to line up in one row such that distances from the light emitting diodes to a checking region are equal in a state of being inclined with respect to a surface of the checking region, and the light emitting sections in the second illuminating group include light emitting diodes, respectively, that are arranged to line up in one row such that distances from the light emitting diodes to the checking region are equal in a state of being inclined with respect to the surface of the checking region.

7. The apparatus for checking the adherence state of fiber reinforced plastic tape according to claim 1, wherein the illuminating section is provided in a plurality of opening sections that are provided in a part of a casing, the light emitting sections in the first illuminating group and the light emitting sections in the second illumination are formed, respectively, by connecting one ends of branched optical fibers with the opening sections, the light emitting sections in the first illuminating group are arranged to line up in one row such that distances from the light emitting sections to a checking region are equal in a state of being inclined with respect to a surface of the checking region, and the light emitting sections in the second illuminating group are arranged to line up in one row such that distances from the light emitting sections to the checking region are equal in a state of being inclined with respect to the surface of the checking region.

8. The apparatus for checking the adherence state of fiber reinforced plastic tape according to claim 1, wherein the illuminating section is provided in a plurality of opening sections that are provided in a part of a casing, the light emitting sections in the first illuminating group and the light emitting sections in the second illumination are formed, respectively, by connecting one ends of branched optical fibers with the opening sections, the light emitting sections in the first illuminating group are arranged to line up in one row such that distances from the light emitting sections to a checking region are equal in a state of being inclined with respect to a surface of the checking region, and the light emitting sections in the second illuminating group are arranged to line up in one row such that distances from the light emitting sections to the checking region are equal in a state of being inclined with respect to the surface of the checking region.

9. The apparatus for checking the adherence state of fiber reinforced plastic tape according to claim 1, wherein the illuminating section is provided in a plurality of opening sections that are provided in a part of a casing, the light emitting sections in the first illuminating group and the light emitting sections in the second illumination are formed, respectively, by connecting one ends of branched optical fibers with the opening sections, the light emitting sections in the first illuminating group are arranged to line up in one row such that distances from the light emitting sections to a checking region are equal in a state of being inclined with respect to a surface of the checking region, and the light emitting sections in the second illuminating group are arranged to line up in one row such that distances from the light emitting sections to the checking region are equal in a state of being inclined with respect to the surface of the checking region.

* * * * *